United States Patent [19]

Herring

[11] 4,176,667

[45] Dec. 4, 1979

[54] DISPOSABLE LIQUID ABSORBENT PAD AND METHOD

[75] Inventor: Julian N. Herring, Greenwood, S.C.

[73] Assignee: Adult Care Products, Inc., Greenwood, S.C.

[21] Appl. No.: 845,377

[22] Filed: Oct. 25, 1977

[51] Int. Cl.$^2$ ............... A61F 13/16; A61L 15/00; A61F 13/00

[52] U.S. Cl. ............... 128/287; 128/290 R; 128/156; 128/296

[58] Field of Search ............... 128/155, 156, 270, 280, 128/284, 287, 288, 289, 290 P, 290 B, 290 W, 290 R, 29.6; 428/175, 176, 152, 153, 211

[56] References Cited

U.S. PATENT DOCUMENTS

| | | | |
|---|---|---|---|
| 2,916,037 | 11/1956 | Hansen | 128/284 |
| 3,563,243 | 2/1971 | Lindquist | 128/287 |
| 3,664,343 | 5/1972 | Assarsson | 128/284 |
| 3,686,024 | 8/1972 | Nankee et al. | 428/286 |
| 3,888,257 | 6/1975 | Cook et al. | 128/296 |
| 3,926,891 | 12/1975 | Gross et al. | 260/29.6 E |
| 4,035,217 | 7/1977 | Kennette et al. | 156/279 |

Primary Examiner—Robert W. Michell
Assistant Examiner—Thomas J. Wallen
Attorney, Agent, or Firm—Bailey, Dority & Flint

[57] ABSTRACT

A disposable liquid absorbent pad is illustrated wherein a wicking sheet of creped paper is utilized for supporting a cast film of acrylic polymer capable of forming a gel upon application of liquid thereto, there being a direct mechanical connection between the ridged surfaces of the creped paper and the film, and preferably voids between the ridges of the wicking sheet. The film is laminated to the creped wicking sheet by moistening one surface of the film as by a spray mist of liquid and then applying the resulting gel or tacky side to the ridges of the creped sheet. The product thus formed is suitable for use adjacent the human body and has particular application for use as diapers, underpads and bandages or wherever the absorption of liquids quickly and in relatively large amounts is desirable.

3 Claims, 4 Drawing Figures

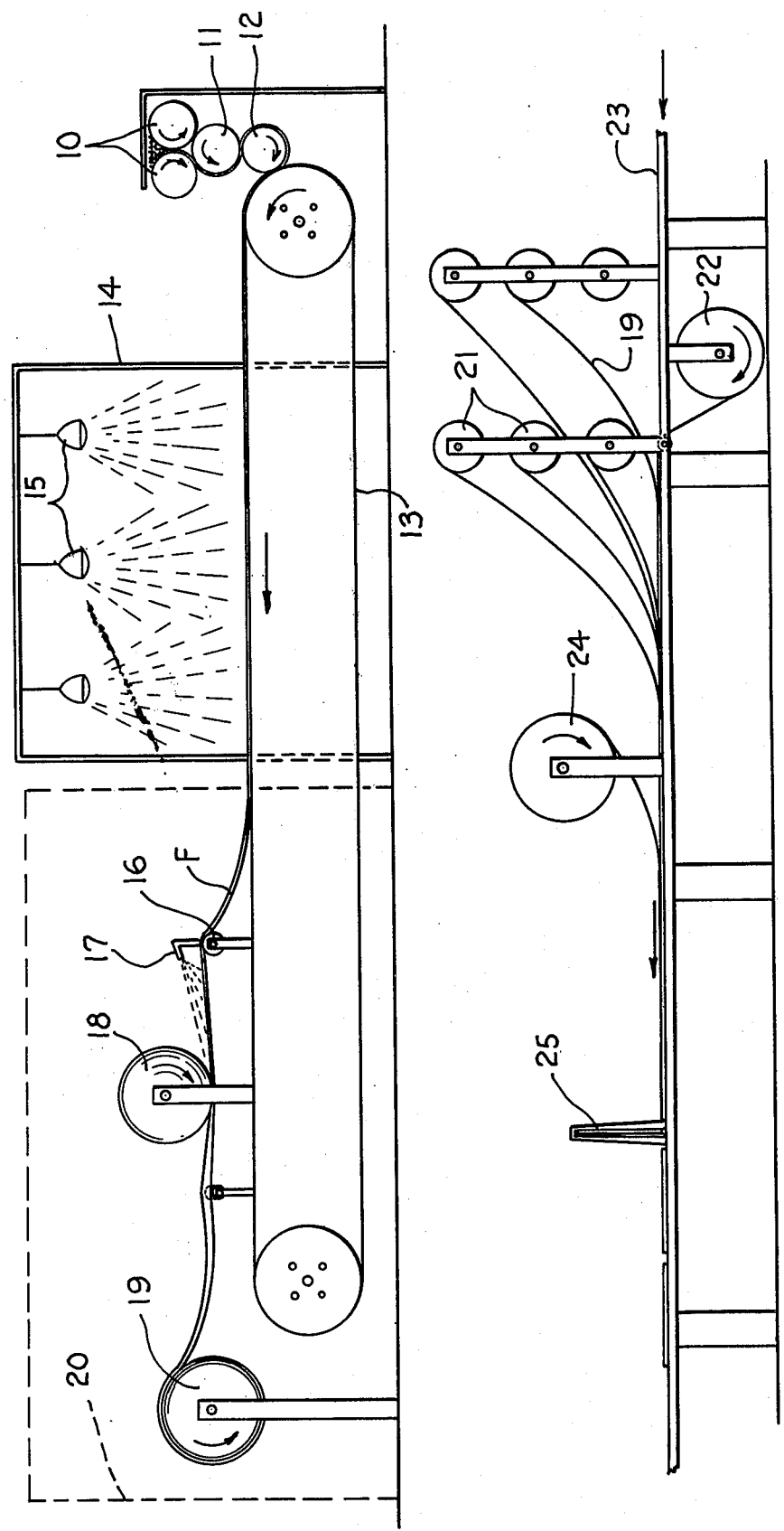

DISPOSABLE LIQUID ABSORBENT PAD AND METHOD

BACKGROUND OF THE INVENTION

There are numerous disposable articles in the form of diapers, bandages and the like available on the market and such are familiar and readily available for household use. There are as well, a large variety of disposable absorbent pads used in institutions such as hospitals including bandages and underpads, as well as adult and junior diapers. For example U.S. Pat. No. 3,888,257 illustrates a disposable absorbent article useful for the same general purposes as the articles constructed in accordance with the present invention utilizing a powdered polymer dispersed in a substrate. U.S. Pat. No. 3,563,243 illustrates an absorbent pad for similar uses wherein crepe cellulose tissue is utilized in contact with the surface of a hydrophilic foam sheet.

Suitable acrylic resins for forming films useful in the practice of the present invention are illustrated in U.S. Pat. Nos. 3,926,891 and 4,026,932 the disclosure of which are incorporated herein and made a part thereof by reference. Such acrylic resins are supplied by The Dow Chemical Company of Midland, Michigan, and a specific preferred composition is designated as acrylic polymer XD-8587.01. Such polymers when employed in connection with suitable amounts of water, catalyst and surfactant may be cast into a film suitable for use in the present invention.

SUMMARY OF THE INVENTION

It has been found that a highly absorbent film, such as manufactured utilizing such available waterswellable gel forming crosslinked polyacrylate polymers as described above, may be more effectively utilized when laminated to a creped substrate without the use of adhesive by a method wherein a mechanical connection is achieved between the ridges of the creped material and a surface of the film. This product preferably contemplates the leaving of voids between the mechanical connections between the ridges and the film. The method of lamination contemplates utilizing a controlled amount of liquid as by a fine mist to limit the extent to which a gel is formed upon the surface of the film during the process of laminating the film to the creped substrate. It has further been found that such a pad may be useful in forming diapers, underpads, sanitary napkins and bandages and the like in accordance with the various constructions utilized in the prior art wherein the pad of the present invention is sandwiched between a bottom sheet such as an imperforate backing member and a cover or top sheet with any number or types of filler material utilized as may be best indicated for the desired purposes. It is especially useful to seal the edges of the assembed layers of material along the edges utilizing broader widths than lengths of material. For example, the material is cut narrow in the machine direction thus causing the ridges of the creped or wrinkled sheet material to extend in the widest direction so as to direct the flow of liquid which may be applied thereto in use toward the sealed edges.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein:

FIG. 1 is a schematic side elevation illustrating the method of casting film and laminating the film to a creped substrate in accordance with the method of the present invention, FIG. 2 is a schematic side elevation illustrating the steps of utilizing the absorbent pad constructed in accordance with the present invention in the formation of a diaper or underpad.

DESCRIPTION OF A PREFERRED EMBODIMENT

Figure 3:
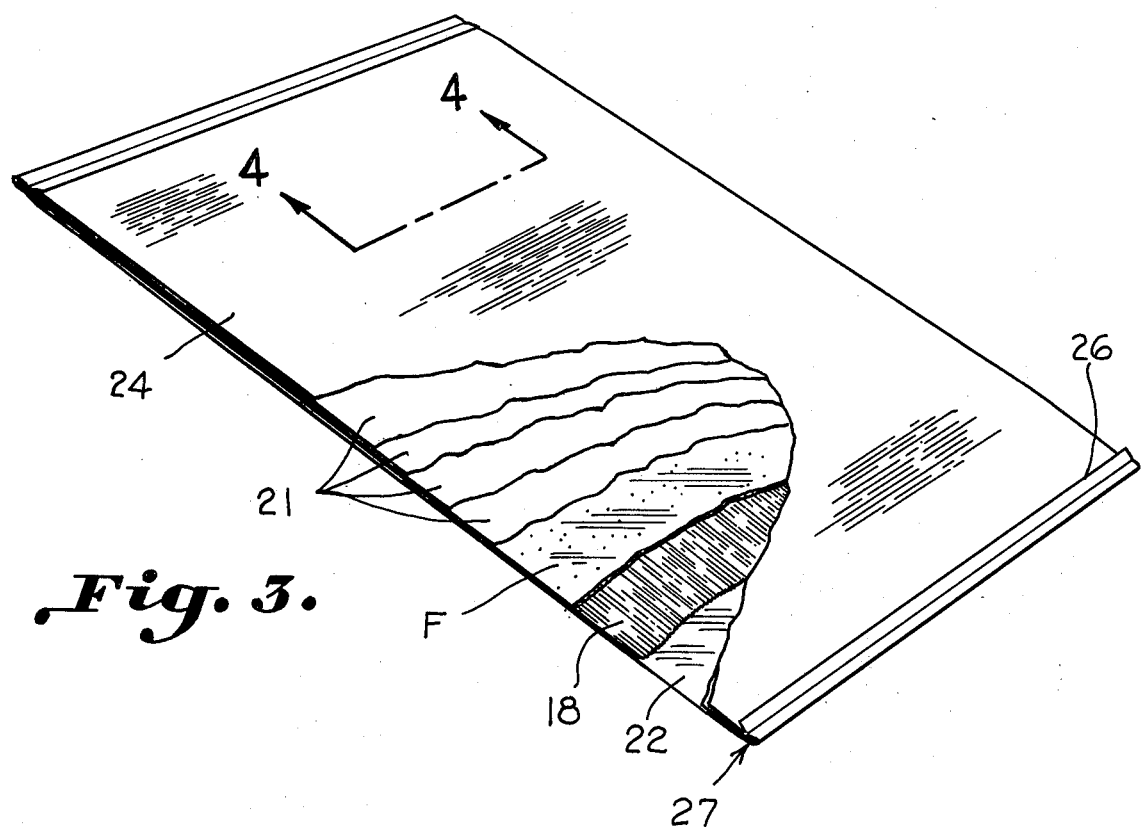
FIG. 3 is a perspective view illustrating a diaper or underpad constructed in accordance with the present invention utilizing the absorbent pad described herein.

A suitable composition for the casting of the film has been found to include acrylic polymer XD-8587.01 at 94 parts solids by weight, 1 part solids by weight of Hercules Polycup 172 catalyst, and 5 parts solids by weight of ICI Tween 20 surfactant. If increased absorbing capacity is desired in the film the Polycup 172 may be reduced to 0.6 parts solids by weight and the acrylic polymer XD-8587.01 increased to 94.4 parts solids by weight.

Referring especially to FIG. 1, and starting at the right hand end, the composition including polymer together with water catalyst and surfactant is passed between stainless steel metering rolls designated at 10. The metering rolls deliver the liquid composition to a stainless steel roll 11 which turns in a counter-clockwise direction which transfers the composition to a rubber roll 12, which turns in a clockwise direction prior to passing the partially formed film to a silicone coated stainless steel continuous belt 13. The conveyor maintains the belt moving the the direction of the arrow in FIG. 1 and the material carried thereby is passed through an oven or range 14 which has heaters schematically illustrated at 15. The belt moves at speeds up to 80 feet per minute and may be about 80 feet in length on the upper run thereof. The range 14 is heated to approximately 225° F. and heat is forced onto the material carried by the belt 13 as by suitable fans (not shown). The range itself may be approximately 45 feet in length.

At this stage the film has been formed and is carried by the belt until the casting of the film is completed when about eighty-five percent or more of the water has been driven off by the range 14. The cast polymer film F is now lifted from the belt in a high humidity area to keep the film flexible. The film is lifted by passage over a spreader bar 16 after which water in a fine mist is applied thereto as by sprayer nozzles 17. By thus controlling the application of the liquid to one side of the film F, that side is made tacky by at least partial gel formation whereas the other side of the film remains in cast form.

Creped paper which is highly creped or wrinkled, may be in the form of 23 pound basis weight tissue. When the two meet the tackiness of the polymer film laminates the two surfaces where they meet but leaves pockets of unlaminated film tissue to help in allowing more surface area of the polymer, therefore facilitating faster absorption of fluid. The creped paper is supplied in open width from the roll of creped paper 18 and the product thus laminated is packaged in rolls 19. The polymer film tissue laminate is slit to the correct width and rolled into the large rolls 19 which may preferably be wrapped in polyethylene to insure maintenance of the proper moisture level. Also, preferably, the product area during the lamination described above is preferably enclosed by polyethylene drapes 20 to maintain a humidity level of about seventy percent while running.

FIG. 2 illustrates the formation of a disposable article such as an adult diaper illustrated in greater detail in FIG. 3. Suitable roll stands are utilized for supplying filler tissue from a desired number of rolls as designated at 21. The polyethylene backing material is brought up from a roll 22 and is positioned in a first position next adjacent a moving belt conveyor 23. The laminated material 19 including the film F and tissue 18, as well as various filler tissues 21 are then applied thereupon and cover material is applied from the roll 24 on top of the layers thus stacked. The polyethylene material may then be turned over the stack at the edges and the entire assembly secured together as by gluing. The diapers or underpads are then severed in desirable lengths as by a guillotine knife 25. The lengths as stated above, are of a lesser length dimension preferably than the width in order to supply a product wherein the substantially longitudinal creped portions pass across the article widthwise directing the flow of liquid toward the sealed edges.

The sealed edges are illustrated in the disposable product illustrated in FIG. 3 and the fold of the polyethylene sheet is illustrated at 26. The layers may be suitably adhesively secured together as illustrated generally at 27 in any desirable fashion. The polyethylene backing layer is designated at 22 and is preferably of imperforate material such as polyethylene. The laminated product in accordance with the present invention is illustrated as including the film F as well as the corrugated sheet material designated at 18. Several layers of tissue of filler material are designated at 21, and a suitable cover sheet, which may be of wet strength tissue, print bonded. Rayon non-woven, spun bonded propylene or any other suitable material is designated at 24.

Figure 4:
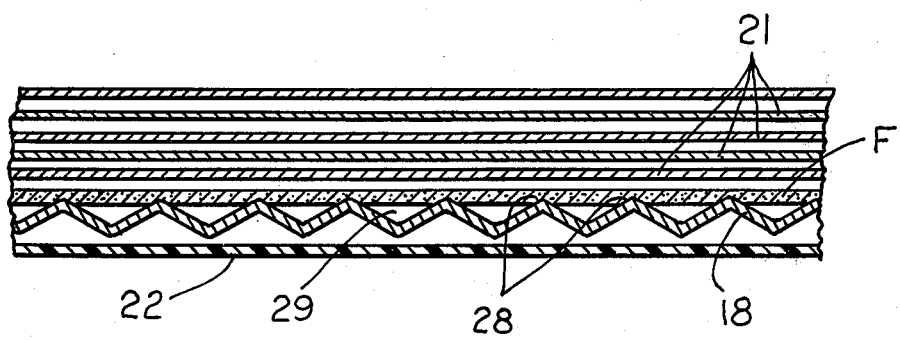
FIG. 4 is an enlarged transverse sectional elevation taken on the line 4—4 in FIG. 3.

By reference to FIG. 4, it will be noted that the film F is mechanically bonded at the apex of the raised portion as by the apex portions penetrating into the moistened portion of the film and such mechanical junctures are designated at 28. It will also be noted that voids are provided or left at 29 adjacent the valleys formed within the creped substrate. The film may be about 1.8 mils in thickness and may be placed film side up as shown or if two thicknesses of laminate are used, one of the film sides may be down as desired.

Thus, a free film may be bonded to a wicking sheet so that it may be handled in manufacturing in a variety of disposable products while at the same time increasing the rate of liquid takeup.

While a preferred embodiment of the invention has been described using specific terms, such description is for illustrative purposes only, and it is to be understood that changes and variations may be made without departing from the spirit or scope of the following claims.

What is claimed is:

1. The method of making a disposable liquid absorbent pad for use as a diaper sanitary napkin and the like comprising the steps of:
   forming a film of polymeric material capable of forming a gel upon application of liquid thereto;
   providing a crinkled absorbent sheet having apex portions for receiving said film thereacross; and
   producing a controlled amount of gel on said film forming a limited bond with said sheet at the apex portions facilitating wicking of liquid applied to the pad thus formed through voids between apex portions of said crinkled absorbent sheet.

2. The method set forth in claim 1 including interposing said pad between a topsheet and a bottomsheet.

3. The method set forth in claim 1 including spraying a limited amount of liquid for producing said controlled amount of gel on said film.

* * * * *

Notice of Adverse Decision in Interference

In Interference No. 100,933, involving Patent No. 4,176,667, J. N. Herring, DISPOSABLE LIQUID ABSORBENT PAD AND METHOD, final judgment adverse to the patentee, was rendered Aug. 30, 1983, as to claims 1 and 3.

[*Official Gazette November 15, 1983.*]